(12) United States Patent
Huang et al.

(10) Patent No.: US 12,310,952 B2
(45) Date of Patent: May 27, 2025

(54) **TRADITIONAL CHINESE DRUG MONOMER COMPOSITION FOR TREATING *HELICOBACTER PYLORI*, PREPARATION METHOD AND USE THEREOF**

(71) Applicant: YOUJIANG MEDICAL UNIVERSITY FOR NATIONALITIES, Guangxi (CN)

(72) Inventors: Yanqiang Huang, Guangxi (CN); Rujia Li, Guangxi (CN)

(73) Assignee: YOUJIANG MEDICAL UNIVERSITY FOR NATIONALITIES, Guangxi (CN)

( * ) Notice: Subject to any disclaimer, the term of this patent is extended or adjusted under 35 U.S.C. 154(b) by 103 days.

(21) Appl. No.: 18/190,072

(22) Filed: Mar. 25, 2023

(65) Prior Publication Data
US 2024/0316013 A1    Sep. 26, 2024

(51) Int. Cl.
| | | |
|---|---|---|
| *A61K 31/4375* | (2006.01) | |
| *A61K 31/343* | (2006.01) | |
| *A61K 31/4355* | (2006.01) | |
| *A61P 31/04* | (2006.01) | |

(52) U.S. Cl.
CPC ........ *A61K 31/4375* (2013.01); *A61K 31/343* (2013.01); *A61K 31/4355* (2013.01); *A61P 31/04* (2018.01)

(58) Field of Classification Search
CPC .... A61K 31/4375; A61K 31/343; A61P 31/04
USPC ....................................................... 514/279
See application file for complete search history.

(56) References Cited

FOREIGN PATENT DOCUMENTS

| CN | 111905017 | | 11/2020 |
| CN | 113855737 | | 12/2021 |
| CN | 113975326 A | * | 1/2022 |
| CN | 114522169 | | 5/2022 |

OTHER PUBLICATIONS

Luo et al., Dihydrotanshinone I Is Effective against Drug-Resistant Helicobacter pylori In Vitro and In Vivo, Mar. 2021, Antimicrobial Agents and Chemotherapy, vol. 65 (3), pp. 1-2 (Year: 2021).*
Li et al., Application of traditional Chinese medicine in treatment of Helicobacter pylori infection, Dec. 16, 2021, World J Clin Cases, vol. 9(35), pp. 10781-10791 (Year: 2021).*
Zhou et al., Inhibition of Helicobacter pylori and Its Associated Urease by Palmatine: Investigation on the Potential Mechanism, Jan. 3, 2017, PLoS One, vol. 12(1) e0168944, pp. 1-15 (Year: 2017).*
Luo et al., Dihydrotanshinone I is Effective against Drug-Resistant Helicobacter pylori In Vitro and In Vivo, Mar. 2021, Antimicrobian Agents and Chemotherapy, vol. 65(3), pp. 1-2 (Year: 2021).*
Wang Xiao-Xial et al., "Chemical constituents from fruits of Euodia rutaecarpa", Chinese Traditional and Herbal Drugs, vol. 44, No. 10, with English abstract, May 31, 2013, pp. 1241-1244, abstract only.
Office Action of China Counterpart Application, with English translation thereof, issued on Jul. 21, 2022, pp. 1-14.

* cited by examiner

*Primary Examiner* — Jeffrey H Murray
*Assistant Examiner* — Rilla Marie Samsell
(74) *Attorney, Agent, or Firm* — JCIPRNET

(57) ABSTRACT

A traditional Chinese drug monomer composition for treating *Helicobacter pylori* and its preparation method and use thereof, the steps are: a. dissolving drugs: dissolving berberine, evolitrine, and tanshinone I respectively in absolute ethanol; b. combining the drugs: mixing an ethanol solution obtained from the step a according to the mass ratio of berberine, evolitrine, and tanshinone I at 6:1:(0.75-6) to obtain the composition. The present disclosure successfully prepares a traditional Chinese drug monomer composition for the treatment of *Helicobacter pylori*, which has an extremely obvious inhibitory effect on *Helicobacter pylori* both in vivo and in vitro, and has a specific effect, low toxicity, and is not easy to produce drug resistance.

4 Claims, 5 Drawing Sheets

TRADITIONAL CHINESE DRUG MONOMER COMPOSITION FOR TREATING *HELICOBACTER PYLORI*, PREPARATION METHOD AND USE THEREOF

BACKGROUND

Technical Field

The present disclosure relates to the field of drug, and in particular to a traditional Chinese drug monomer composition for treating *Helicobacter pylori*, a preparation method and a use thereof.

Description of Related Art

*Helicobacter pylori* (Hp) is a kind of bacteria that can continuously colonize human gastric mucosa and cause gastric infection, which is related to a variety of gastrointestinal diseases. At present, the eradication of Hp in the world is mainly treated with antibiotics combined with bismuth agents, antimicrobial agents mainly include metronidazole, clarithromycin, levofloxacin, and the like. However, with the widespread use and abuse of antibiotics, the drug resistance of Hp is getting higher and higher, and the eradication rate is also getting lower and lower, which seriously threatens the health and safety of the public. The treatment of Hp with traditional Chinese drugs has many advantages such as a definite curative effect, not easy to produce a drug resistance, a low toxicity and a high eradication rate. However, the effective monomer components of many traditional Chinese drug antibacterial agents are not yet clear. Even if the effective monomer components of traditional Chinese drug are found, sometimes they are effective in vitro, but may not be effective in vivo, which requires a further experimental verification.

Our study on the screening of antibacterial components of traditional Chinese drug has found that the main components for inhibiting Hp in *Coptis chinensis, Evodia rutaecarpa, Arctium lappa* and *Salvia* miltiorrhiza are berberine, evolitrine, and tanshinone I, respectively, the MICs are 16-32 μg/mL, 16-32 μg/mL, and 0.5-1 μg/mL, respectively, and the mechanisms of these monomers are different. The combination of different monomer compositions can resist bacteria, increase the action target of the composition, be conducive to improve the antibacterial effect and reduce the drug resistance of the composition. Therefore, in the present disclosure, according to the quality ratio of Zuojin pills, berberine, evolitrine, and tanshinone I are combined according to a certain quality ratio to inhibit Hp. This combination can synergistically enhance the inhibition of Hp, and is not easy to produce drug resistance, which has an extremely excellent effect on the treatment of Hp infection related diseases.

A method of preparing traditional Chinese drug monomer combination involved in the present disclosure has not been reported. This combination has a specific inhibitory effect on Hp in vivo and in vitro, can better promote the repair of gastric mucositis in mice with acute gastritis infected by Hp, is not easy to produce a drug resistance, and has a high safety, which can be used as a candidate drug for treating diseases related to Hp infection, and the use of which is disclosed for the first time.

SUMMARY

The technical problems solved are that: in order to enhance the inhibitory activity of traditional Chinese drug on Hp, the present disclosure provides a traditional Chinese drug monomer composition for the treatment of Hp and its preparation method and use. The composition prepared by the method has a good inhibitory effect on drug-resistant and sensitive Hp, and the antibacterial effect and therapeutic effect are significantly improved.

The following technical solutions are as follows: provided is a method of preparing a traditional Chinese drug monomer composition for treating Hp. The steps are as follows: a. drugs are dissolved: berberine, evolitrine, and tanshinone I are respectively dissolved in absolute ethanol; b. the drugs are combined: an ethanol solution obtained from the step a is combined according to berberine, evolitrine, and tanshinone I at 6:1:(0.75-6) to obtain the composition.

The mass ratio of berberine, evolitrine, and tanshinone I is 6:1:3.

Provided is a traditional Chinese drug monomer composition prepared according to the above method.

Provided is a use of the traditional Chinese drug monomer composition in a preparation of a drug for treating Hp infection related diseases.

Provided is a drug for treating Hp infection related diseases, and an effective component is the traditional Chinese drug monomer composition.

The beneficial effects of the present disclosure are that: Firstly, the present disclosure successfully prepares the composition; Secondly, the composition prepared by the present disclosure is used to inhibit the growth of Hp, and has a high specificity, a low toxic side effect, and is not easy to produce a drug resistance, which can be used as a candidate drug to treat Hp infection, and effectively alleviate the severe drug resistance problem of Hp.

DESCRIPTION OF THE EMBODIMENTS

Example 1

Figure 1:
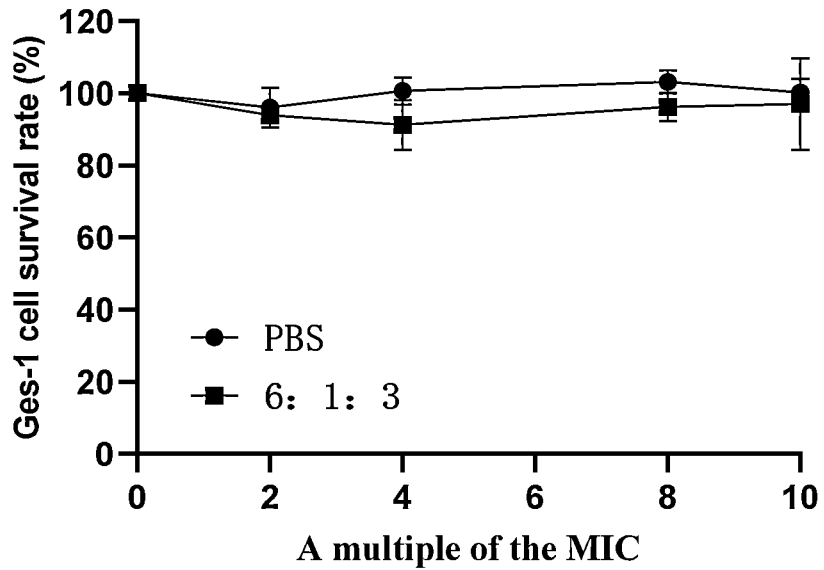
FIG. 1 illustrates a cytotoxicity evaluation of the 6:1:3 composition on cells.
Figure 1:
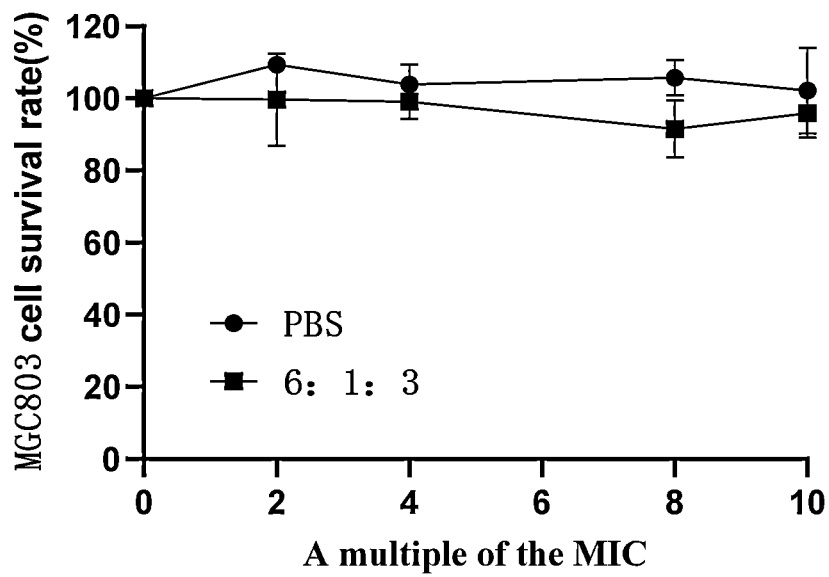

In Step 1, drugs are dissolved: berberine, evolitrine, and tanshinone I are respectively weighed and dissolved in absolute ethanol, so that the final concentration is 4 mg/mL.

In Step 2, the drugs are combined: the berberine, evolitrine, and tanshinone I are mixed according to different mass ratios of 6:1:0.75 to obtain the composition 1.

Example 2

In Step 1, drugs are dissolved: berberine, evolitrine, and tanshinone I are respectively weighed and dissolved in absolute ethanol, so that the final concentration is 4 mg/mL.

In Step 2, the drug are combined: the berberine, evolitrine, and tanshinone I are mixed according to different mass ratios of 6:1:1.5 to obtain the composition 2.

Example 3

In Step 1, drugs are dissolved: berberine, evolitrine, and tanshinone I are respectively weighed and dissolved in absolute ethanol, so that the final concentration is 4 mg/mL.

In Step 2, the drugs are combined: the berberine, evolitrine, and tanshinone I are mixed according to different mass ratios of 6:1:3 to obtain the composition 3.

Example 4

In Step 1, drugs are dissolved: berberine, evolitrine, and tanshinone I are respectively weighed and dissolved in absolute ethanol, so that the final concentration is 4 mg/mL.

In Step 2, the drugs are combined: the berberine, evolitrine, and tanshinone I are mixed according to different mass ratios of 6:1:6 to obtain the composition 4.

Example 5

In Step 1, drugs are dissolved: berberine, evolitrine, and tanshinone I are respectively weighed and dissolved in absolute ethanol, so that the final concentration is 4 mg/mL.

In Step 2, the drugs are combined: the berberine, evolitrine, and tanshinone I are mixed according to different mass ratios of 6:1:5.5 to obtain the composition 5.

The inhibitory effect of the present disclosure on *Helicobacter pylori* is further described in detail by the following examples.

1. Material
1.1 Sample
The compositions 1, 2, 3, 4 and 5 are prepared according to Examples 1, 2, 3, 4 and 5, respectively.
1.2. Strain
(1) *Helicobacter pylori* strains: standard strains 26695, NSH57, MSD132 and G27 are presented by Dr. Hongkai Bi of Nanjing Medical University; clinical metronidazole drug-resistant strains, clarithromycin drug-resistant strains, levofloxacin drug-resistant strains, levofloxacin and metronidazole drug-resistant strains, clarithromycin and metronidazole drug-resistant strains, levofloxacin and clarithromycin and metronidazole multi drug-resistant strains (HPBS001, HPBS002, HPBS003, and the like) are provided by the Research Center for the Prevention and Treatment of Drug Resistant Microbial Infections of Youjiang Medical University for Nationalities.
(2) Non *Helicobacter pylori* strains: *Staphylococcus aureus, Escherichia coli, Pseudomonas aeruginosa, Acinetobacter baumannii, Klebsiella pneumoniae, Candida albicans, Enterobacter cloacae, Campylobacter jejuni, Bacillus subtilis, Proteus mirabilis, Lactobacillus campylobacter, Stenotrophomonas maltophilia, Morganella morganii, Candida tropicalis, Staphylococcus haemolyticus, Acetobacter, Saccharomyces cerevisiae, Enterobacter hormaechei* well is provided by the Research Center for the Prevention and Treatment of Drug Resistant Microbial Infections of Youjiang Medical University for Nationalities.

1.3 Main culture media and reagents: Columbia culture medium, Brain Heart Infusion Broth, nutrient agar culture medium, nutrient broth culture medium, MH culture medium, Sabouraud culture medium, standard calf serum.
1.4 Main instruments: three gas incubator, centrifuge, microplate reader, electronic balance, and the like.
1.5 Consumable materials: EP tube, tip, centrifuge tube, and the like.
2. Method and Results
2.1 Chessboard method is used to detect the synergistic inhibitory effect of the mixture of two traditional Chinese monomers on *Helicobacter pylori* (FIC, 100 μL system).
(1) The ethanol solution of berberine, evolitrine, and tanshinone I with the concentration of 4 mg/mL is prepared for a subsequent use.
(2) The preparation of MIC plate: in Step 1, a culture medium of 167.2 μL is added to well B1 and well A2 on 96 well plate, and then antibacterial drugs of 12.8 μL are added to the well B1 and the well A2, respectively, a culture medium of 90 μL is added to other wells, the drugs are diluted sequentially from A2 to A12, B1 to H1; in Step 2, the culture medium of 90 μL is added to A2 to A12 and B1 to H1, respectively; in Step 3, the drugs are diluted longitudinally from A to H firstly, and then diluted transversely from 1 to 12.
(3) The preparation of bacterial solution: *Helicobacter pylori* growing in logarithmic phase on the solid plate is taken and BHI culture medium is used to prepare bacterial suspension. The concentration $OD_{600}$ is adjusted to $0.3(1\times10^8$ CFU/mL), and the bacterial suspension is diluted 10 times to $1\times10^7$ CFU/mL for a subsequent use.
(4) The Inoculation of bacterial solution: The bacterial solution of 10 μL is taken and add into every well except A1 well (the concentration of bacterial solution in each well is about $1.0\times10^6$ CFU/mL), and cultured for 72 hours to determine the results.
(5) Result Determination: The MIC is the lowest drug concentration that completely inhibits the growth of bacteria in the wells. A formula is used to calculate FIC, the formula is FIC=MICA/A+MICB/B (FIC: fractional inhibitory concentration), where A and B are the MIC values of the two drugs when they are used alone, MICA and MICB are the MIC values of the two drugs when they are used in combination, and FIC≤0.5 is determined as a synergistic effect; 0.5<FIC≤1 is determined as an additive effect; 1<FIC≤2 is determined as an irrelevant effect; FIC>2 is determined as antagonistic effect, and each drug is repeated three times.
(6) Results: The combination of evolitrine and berberine is the synergistic effect, the combination of and tanshinone I is the irrelevant effect, and the other combinations are the additive effect. The results are as shown in Table 1.

TABLE 1

FIC (μg/mL) Test through Chessboard Method

| Composition 1(MIC) | Composition 2(MIC) | FIC | Effects |
|---|---|---|---|
| Evolitrine (32 μg/mL) | Berberine (16 μg/mL) | 0.34375 | Synergistic effect |
| Evolitrine (32 μg/mL) | Tanshinone I (1 μg/mL) | 0.7815 | Additive effect |
| Berberine (16 μg/mL) | Tanshinone I (1 μg/mL) | 0.53125 | Additive effect |

2.2 The minimum inhibitory concentration of the composition against *Helicobacter pylori* (MIC, 100 μL system) is detected by a microdilution method.

(1) The ethanol solution of berberine, evolitrine, and tanshinone I with the concentration of 4 mg/mL is prepared, and mixed according to the mass ratio of berberine, evolitrine, and tanshinone I at 6:1:0.75, 6:1:1.5, 6:1:3, 6:1:6 and 6:1:5.5 respectively for a subsequent use.

(2) The preparation of MIC plate: a culture medium of 175 μL is added into the first well of the MIC plate, antibacterial drugs of 5 μL are further added, and then the solution is diluted to the 7-th well in a multiple ratio; no dosing is for the 8-th well, culture medium of 90 μL is kept as the control of adding bacteria without adding drug.

(3) The preparation of bacterial solution: *Helicobacter pylori* growing in logarithmic phase on the solid plate is taken and BHI culture medium is used to prepare bacterial suspension. The concentration $OD_{600}$ is adjusted to $0.3(1\times10^8$ CFU/mL), and the bacterial suspension is diluted 10 times to $1\times10^7$ CFU/mL for a subsequent use.

(4) The inoculation of bacterial solution: The bacterial solution of 10 μL is added to the 1-th to 8-th wells (the concentration of bacterial solution in each well is about $1.0\times10^6$ CFU/mL), and cultured for 72 hours to determine the results.

(5) Result Determination: The MIC is the lowest drug concentration that completely inhibits the growth of bacteria in the wells. The experimental test is meaningful only when the bacteria in the 7-th well (that is, without antibiotics) of the positive control well grow significantly and the 8-th well (without bacterial) does not grow. When a single jumping well occurs in the microdilution method, the highest drug concentration of inhibiting bacterial growth should be recorded. In the case of multiple jumping wells, the results should not be reported and the experimental test should be repeated, and each drug is repeated 3 times.

(6) Results: When the ratio of berberine, evolitrine, and tanshinone I is 6:1:3 (that is, Composition 2), the inhibitory effect on *Helicobacter pylori* is the most obvious. The results are as shown in Table 2.

2.3 The minimum inhibitory concentration of 6:1:3 composition against *Helicobacter pylori* from different sources is detected by the microdilution method (MIC, 100 μL system).

(1) Berberine, evolitrine, and tanshinone I of 4 mg/mL are prepared and mixed at a radio of 6:1:3 for a subsequent use.

(2) The preparation of MIC plate: a culture medium of 175 μL is added into the first well of the MIC plate, antibacterial drugs of 5 μL are further added, and then the solution is diluted to the 7-th well in a multiple ratio; no dosing is for the 8-th well, the culture medium of 90 μL is kept as the control of adding bacteria without adding drug.

(3) The preparation of bacterial solution: *Helicobacter pylori* growing in logarithmic phase on the solid plate is taken and BHI culture medium is used to prepare bacterial suspension. The concentration $OD_{600}$ is adjusted to $0.3(1\times10^1$ CFU/mL), and the bacterial suspension is diluted 10 times to $1\times10^7$ CFU/mL for a subsequent use.

(4) The inoculation of bacterial solution: bacterial solution of 10 μL is added to the 1-th to 8-th wells (the concentration of bacterial solution in each well is about $1.0\times10^6$ CFU/mL), and cultured for 72 hours to determine the results.

(5) Result Determination: The MIC is the lowest drug concentration that completely inhibits the growth of bacteria in the wells. The experimental test is meaningful only when the bacteria in the 7-th well (that is, without antibiotics) of the positive control well grow significantly and the 8-th well (without bacterial) does not grow. When a single jumping well occurs in the microdilution method, the highest drug concentration of inhibiting bacterial growth should be recorded. In the case of multiple jumping wells, the results should not be reported and the experimental test should be repeated, and each drug is repeated 3 times.

(6) Results: When the ratio of berberine, evolitrine, and tanshinone I is 6:1:3, they all have obvious inhibitory effects on sensitive and drug-resistant *Helicobacter pylori*. The results are as shown in Table 3.

TABLE 2

MIC Test of Compositions at Different Ratios

| Berberine | Evolitrine | Tanshinone I | Strains | MIC |
|---|---|---|---|---|
| 6 | 1 | 0.75 | 159 | 2.21 + 0.37 + 0.28 |
| 6 | 1 | 0.75 | 26695 | 2.21 + 0.37 + 0.28 |
| 6 | 1 | 0.75 | G27 | 2.21 + 0.37 + 0.28 |
| 6 | 1 | 1.5 | 159 | 1.88 + 0.31 + 0.47 |
| 6 | 1 | 1.5 | 26695 | 0.94 + 0.16 + 0.23 |
| 6 | 1 | 1.5 | G27 | 1.88 + 0.31 + 0.47 |
| 6 | 1 | 3 | 159 | 0.72 + 0.12 + 0.36 |
| 6 | 1 | 3 | 26695 | 0.72 + 0.12 + 0.36 |
| 6 | 1 | 3 | G27 | 0.72 + 0.12 + 0.36 |
| 6 | 1 | 6 | 159 | 0.49 + 0.08 + 0.49 |
| 6 | 1 | 6 | 26695 | 0.49 + 0.08 + 0.49 |
| 6 | 1 | 6 | G27 | 0.49 + 0.08 + 0.49 |
| 6 | 1 | 5.5 | 159 | 1.44 + 0.24 + 1.32 |
| 6 | 1 | 5.5 | 26695 | 0.72 + 0.12 + 0.66 |
| 6 | 1 | 5.5 | G27 | 1.44 + 0.24 + 1.32 |

TABLE 3

MIC Test of 6:1:3 Composition

| Strain | 6:1:3 |
|---|---|
| 26695 | 0.72 + 0.12 + 0.36 |
| HPBS001 | 0.72 + 0.12 + 0.36 |
| G27 | 0.72 + 0.12 + 0.36 |
| HPBS002 | 0.72 + 0.12 + 0.36 |
| HPBS003 | 0.72 + 0.12 + 0.36 |
| HPBS004 | 0.72 + 0.12 + 0.36 |
| HPBS005 | 1.44 + 0.24 + 0.72 |
| HPBS006 | 1.44 + 0.24 + 0.72 |
| HPBS007 | 0.72 + 0.12 + 0.36 |
| HPBS010 | 0.72 + 0.12 + 0.36 |
| HPBS011 | 0.72 + 0.12 + 0.36 |
| HPBS012 | 0.72 + 0.12 + 0.36 |
| HPBS013 | 0.72 + 0.12 + 0.36 |
| HPBS014 | 1.44 + 0.24 + 0.72 |
| HPBS015 | 0.72 + 0.12 + 0.36 |
| HPBS016 | 1.44 + 0.24 + 0.72 |
| MSD132 | 0.72 + 0.12 + 0.36 |
| NHS57 | 0.72 + 0.12 + 0.36 |

Figure 2:
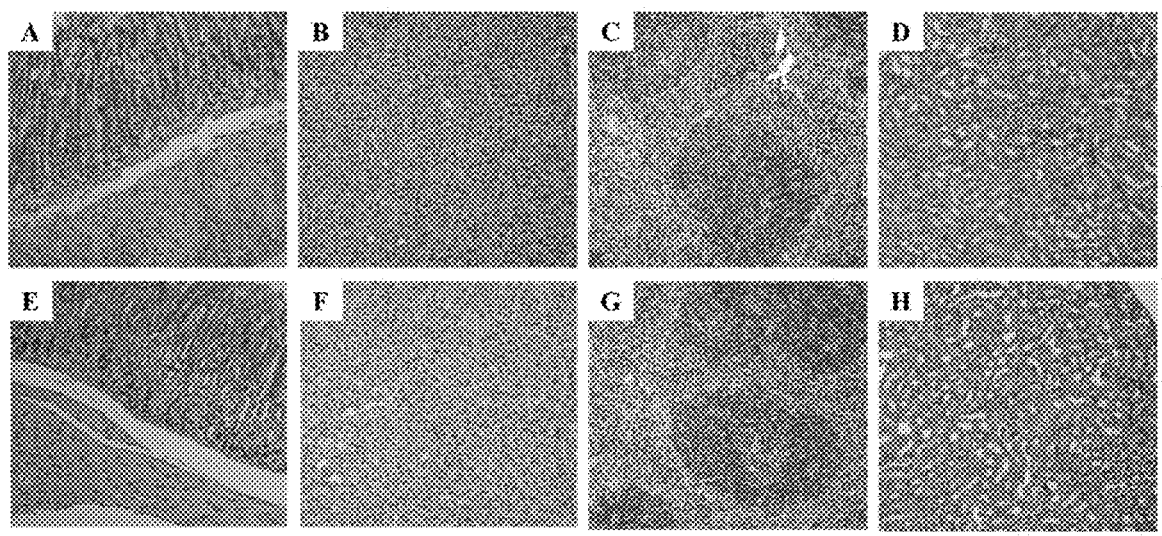
FIG. 2 illustrates tissue injuries of the 6:1:3 composition to the stomachs, livers, spleens and kidneys of mice.

2.2 Drug Toxicity Test
2.2.1 Cytotoxicity Test
(1) Ges-1 and MGC823 cell suspension is prepared, and the concentration is adjusted to $1\times10^5$.
(2) The suspension is inoculated into 96 well plate with 100 μL per well. and the same sample is repeated three times.
(3) The suspension is cultured in a 37° C. incubator for 24 hours.
(4) The composition 3 with different ratios are added, and the group of adding drugs without adding cells is set.
(5) The composition 3 is cultured in the 37° C. incubator for 24 hours.
(6) CCK8 of 10 μL is added, and then cultured for 4 hours after being taped and mixed well.
(7) The absorbance at 450 nm is measured, and the survival rate is calculated according to the formula of cell survival rate=[(As−Ab)]/[(Ac−Ab)]×100%, As are the wells containing cell culture medium, drugs, and CCK-8, Ac are the wells containing cell culture medium, CCK-8, no drug, Ab are the wells containing no cell and drug, only culture medium and CCK-8. The survival curve is established according to the survival rate.
(8) Results: The eight-times MIC of the 6:1:3 composition prepared according to Example 3 has little injury to Ges-1 and BGC823 cells, no significant difference with Zuojin pills, and low toxicity, as illustrated in FIG. 1.
2.2.2 Animal Toxicity Test
(1) The preparation of mice: C57BL/6 mice aged 6 to 8 weeks are purchased and randomly divided into an administered group and the negative control group with 10 mice in each group.
(2) Gavage Administration: The mice are administered 10 times the therapeutic dose, and the therapeutic dose of the composition (6:1:3) is 7 mg/kg, that is, the dosage of the mouse toxicity test is 70 mg/kg, which is administered for 3 consecutive days, once a day; the negative control group is given PBS solution with the same times and amount as the administered group.
(3) Weighing: The mice are weighed from the day before administration for 7 consecutive days.
(4) Efficacy Test: on the third day after drug withdrawal, the mice in the infection group are weighed and their average weight is calculated. Blood is collected from the eyeballs, the mice are sacrificed by dislocation and neck dissection. The stomach, kidney, liver and spleen tissues are taken for pathological sections and H&E staining.
(5) Results: A to D refers to the injury situation of stomach, liver, spleen and kidney in the group of normal mice perfused with PBS, and E to H refers to the injury situation of the gastric gavage composition (6:1:3) to the stomach, liver, spleen and kidney. Compared with the two groups, the prepared composition (6:1:3) is administered 10 times the therapeutic dose, and has no obvious injury to the stomach, liver, spleen and kidney of mice, with extremely low toxicity, as illustrated in FIG. 2.
2.3 The minimum inhibitory concentration (MIC) of the 6:1:3 composition against non-*Helicobacter pylori* is detected by the microdilution method.
(1) The composition (6:1:3) of 4 mg/mL is prepared, and mixed for a subsequent use.
(2) The preparation of MIC plate: a culture medium of 175 μL is added into the first well of the MIC plate. Antibacterial drugs of 5 μL are further added, and then the solution is diluted to the 7-th well in a multiple ratio; no dosing is for the 8-th well, a culture medium of 90 μL is kept as the control of adding bacteria without adding drug.
(3) The preparation of bacterial solution: The bacteria growing in logarithmic phase on the solid plate is taken and the corresponding culture medium is used to prepare bacterial suspension. The concentration of bacteria $OD_{600}$ is adjusted to $0.3(1\times10^8$ CFU/mL), and diluted 100 times to $1\times10^6$ CFU/mL, the concentration of fungus $OD_{600}$ is adjusted to $0.5(5\times10^6$ CFU/mL), and diluted 1000 times to $5\times10^3$ CFU/mL for a subsequent use.
(4) The inoculation of bacterial solution: The bacterial solution of 10 μL is added to the 1-th to 8-th wells (the concentration of bacterial solution in each well is about $1.0\times10^6$ CFU/mL), and cultured for 72 hours to determine the results.
(5) Results Determination: The MIC is the lowest drug concentration that completely inhibits the growth of bacteria in the wells. The experimental test is meaningful only when the bacteria in the 7-th well (that is, without antibiotics) of the positive control well grow significantly and the 8-th well (without bacterial) does not grow. When a single jumping well occurs in the microdilution method, the highest drug concentration of inhibiting bacterial growth should be recorded. In the case of multiple jumping wells, the results should not be reported and the experimental test should be repeated, and each drug is repeated 3 times.
(6) Results: The inhibitory effect of the composition (6:1:3) on most non-*Helicobacter pylori* is relatively poor, indicating that the antibacterial spectrum is relatively narrow, specific, and it is capable of specifically acting on *Helicobacter pylori*, and the results are as shown in Table 3.

TABLE 3

MIC(μg/mL) Test of Prepared 6:1:3 Composition against Non-*Helicobacter pylori*

| Strain | 6:1:3 |
| --- | --- |
| *Proteus mirabilis* | > |
| *Cryptococcus neoformans* | 1.4 + 0.2 + 0.7 |
| *Candida tropicalis* | 11.5 + 1.9 + 5.8 |
| *Bacillus subtilis* | 5.8 + 1.0 + 2.9 |
| *Morganella morganii* | > |
| *Staphylococcus haemolyticus* | > |
| *Stenotrophomonas maltophilia* | > |
| Latin Name *Acetobacter aceti (Pasteur) Beijerinck* | > |
| *Escherichia coli* | > |
| *Lactobacillus curvatus* | > |
| *Enterococcus faecalis* | > |
| *Enterobacter hormaechei* | > |
| *Saccharomyces cerevisiae* | 46.1 + 7.7 + 23.1 |
| *Staphylococcus aureus* | 11.5 + 1.9 + 5.8 |
| *Candida albicans* | 23.1 + 3.8 + 11.5 |
| *Klebsiella pneumoniae* | > |
| *Pseudomonas aeruginosa* | > |
| *Acinetobacter baumannii* | > |

Note: In 6:1:3 group, ">" refers to greater than 46.1+7.7+23.1.

Figure 3:
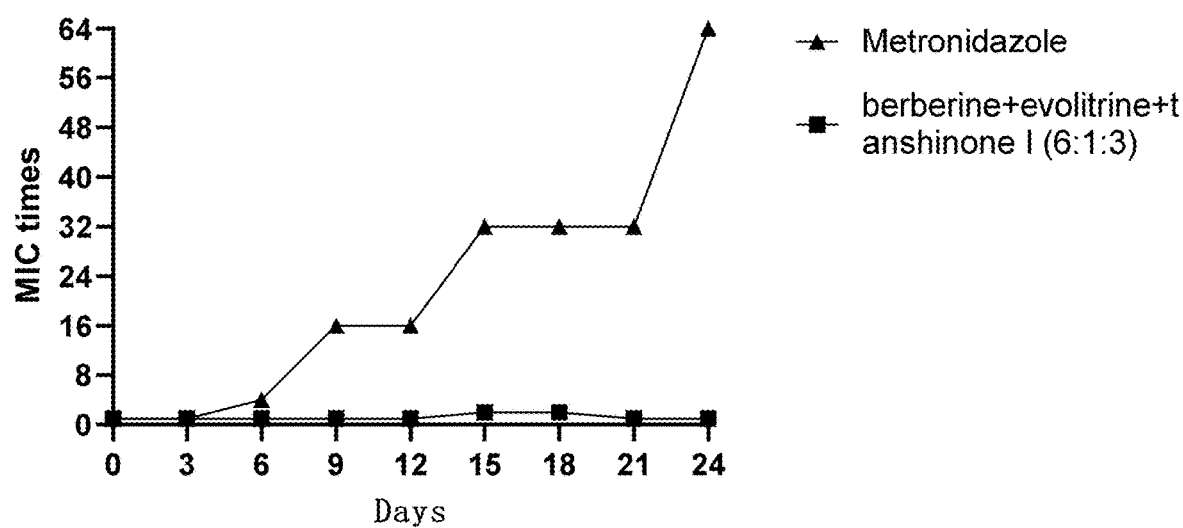
FIG. 3 illustrates an evaluation of the 6:1:3 composition on drug resistance.

2.4 Drug Resistance Test of Prepared 6:1:3 Composition
(1) The drug resistance of phillyrin derivatives is detected with *Helicobacter pylori* G27 strain. Firstly, the MIC of metronidazole and composition (6:1:3) are detected to be 2 μg/mL, 0.72+0.12+0.36 μg/mL respectively, induced with ¼ MIC concentration, detected every 3 days, and induced for 24 days in total. The induced concentration is adjusted with the change of MIC, for example, when the MIC of metronidazole changes to 16 μg/mL, the induced concentration is adjusted to 4 μg/mL.
(2) Results: After 24 days of induction, the resistance to metronidazole is significant, and MIC increases 64 times; the MIC of the prepared 6:1:3 composition has no change and is not easy to develop drug resistance, as illustrated in FIG. 3.

2.5 Animal models are constructed to detect the inhibitory effect of the composition on *H. pylori* in vivo.

Berberine, evolitrine, tanshinone I, omeprazole, amoxicillin and clarithromycin are all dissolved and diluted to 10 mg/mL. Experimental test animals: C57BL/6.

(1) Animal grouping: The experimental test group divides the infection group (BHK159) with a successful modeling into five groups on average, namely, omeprazole+amoxicillin+clarithromycin group (triple therapy group), omeprazole+composition 6:1:3 (7 mg/kg), omeprazole+composition 6:1:3 (7 mg/kg) and PBS group, with 10 mice in each group; 10 mice without *H. pylori* infection are a negative control group.

(2) Animal administration: the experimental group is gavage administration, the group with omeprazole is administrated omeprazole firstly, and then other drugs are administrated 30 minutes later. After the drug is administrated, the mice are fasted for 4 hours; The average weight of mice is 20 g, and the dosage is 138.2 mg/kg of omeprazole, 28.5 mg/kg of amoxicillin, 14.3 mg/kg of clarithromycin, administered once a day for three consecutive times; The negative control group is administrated PBS solution with the same volume and times as above.

Figure 4:
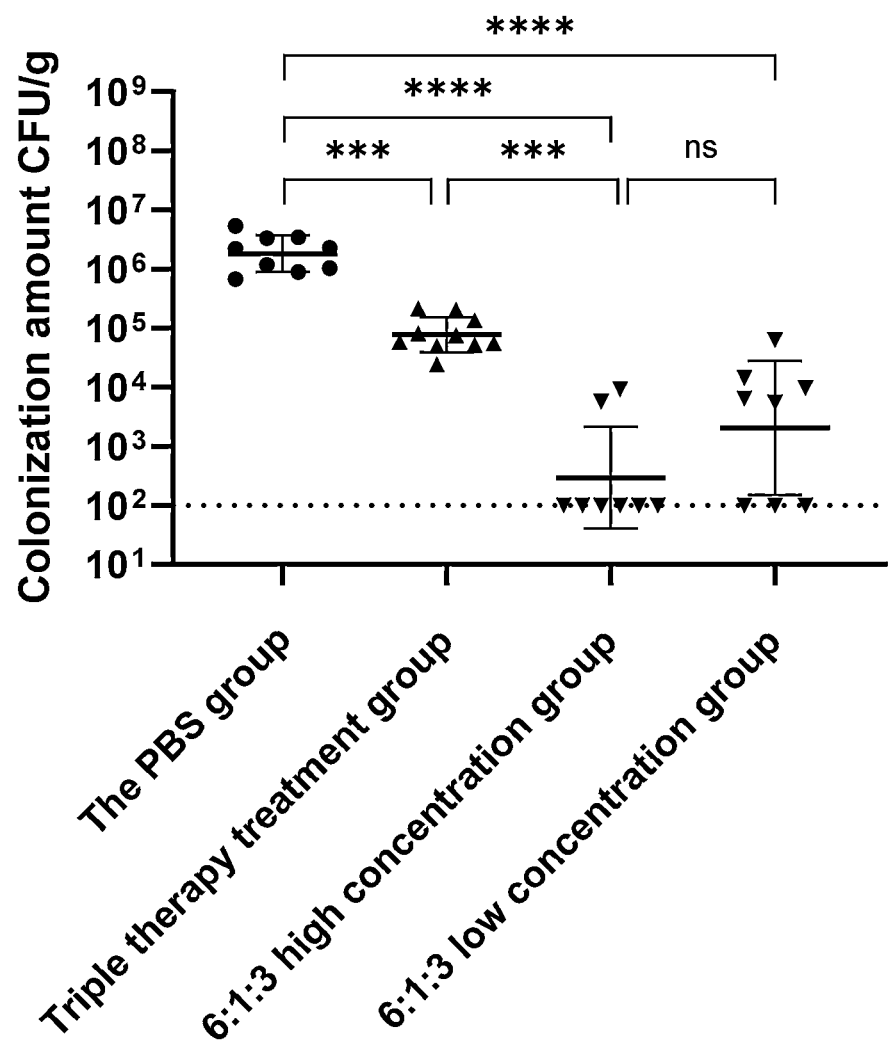
FIG. 4 illustrates an amount of Hp159 colonization after a treatment of acute gastritis mice with the 6:1:3 composition.
Figure 5:
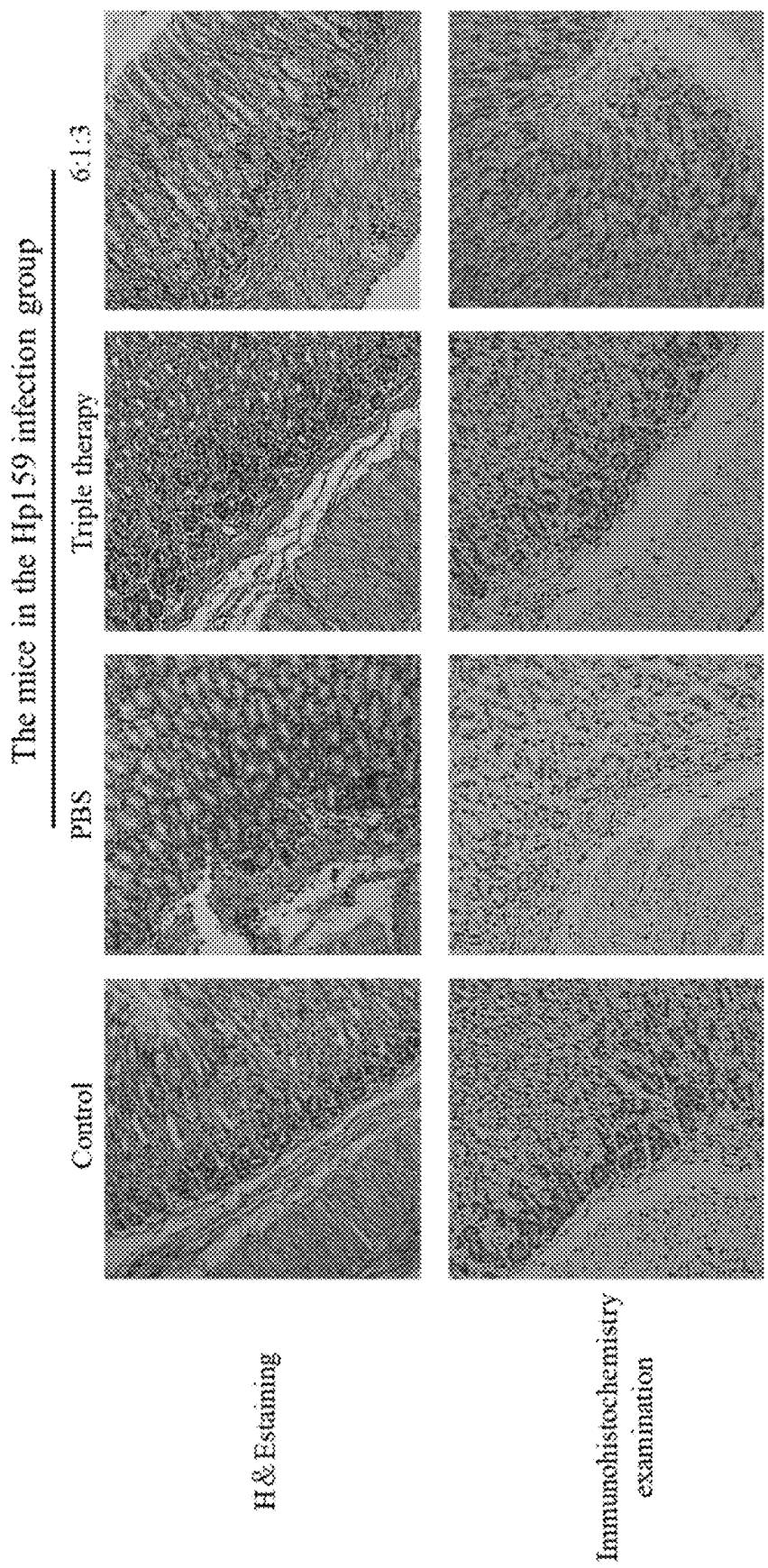
FIG. 5 illustrates a repair situation of gastric mucosa tissue after the treatment of acute gastritis mice with the 6:1:3 composition.
Figure 6:
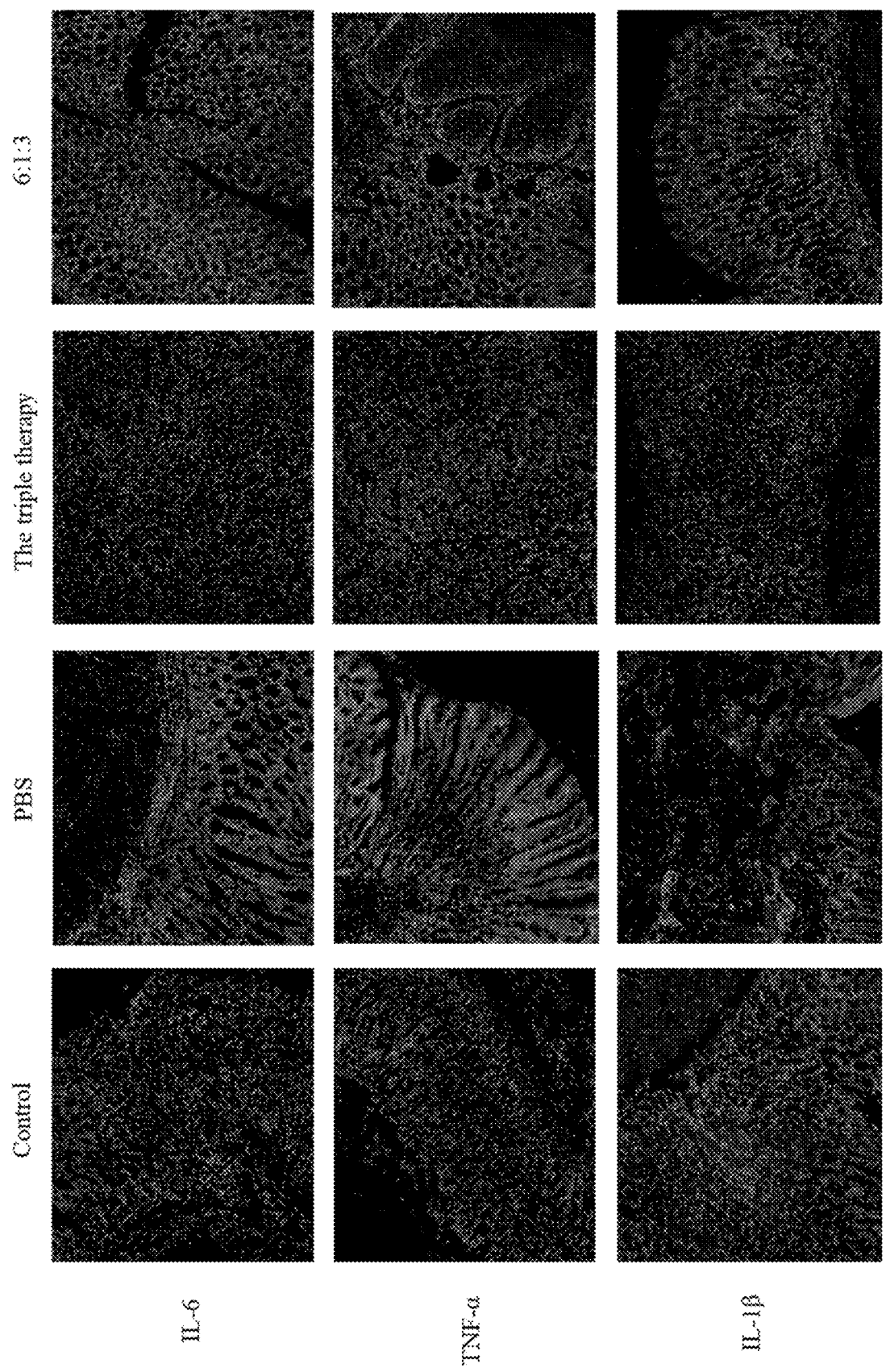
FIG. 6 illustrates a reduction situation of inflammatory factors after the treatment of acute gastritis mice with the 6:1:3 composition.

(3) Efficacy test: On the second day after drug withdrawal, the mice in the infection group are weighed and their average weight is calculated, blood is taken from their eyeballs, their necks are cut, their stomach tissues are taken, broken, and *H. pylori* is isolated, cultured, identified, and the colonization amount is calculated. The therapeutic effect of the group containing 6:1:3 composition is significantly better than that of the triple therapy group and Zuojin pills group, as illustrated in FIG. 4. Some gastric tissues are sectioned with paraffin and examined with H&E staining, TUNEL immunohistochemistry and fluorescence immunoassay. The 6:1:3 composition group has good repair effect on gastric tissues and significantly reduces inflammatory factors, as illustrated in FIG. 5 and FIG. 6.

What is claimed is:

1. A method of preparing a traditional Chinese drug monomer composition for treating *Helicobacter pylori*, wherein steps are:
   a. dissolving drugs: dissolving berberine, evolitrine, and tanshinone I respectively in absolute ethanol;
   b. combining the drugs: mixing an ethanol solution obtained from the step a according to a mass ratio of berberine, evolitrine, and tanshinone I at 6:1:3 to obtain the traditional Chinese drug monomer composition.

2. A traditional Chinese drug monomer composition prepared according to claim 1, wherein a mass ratio of berberine, evolitrine, and tanshinone I is 6:1:3 in the traditional Chinese drug monomer composition, and the traditional Chinese drug monomer composition has inhibitory effect on *Helicobacter pylori* and reduces drug resistance on the *Helicobacter pylori*.

3. A method of using the traditional Chinese drug monomer composition according to claim 2, comprising:
   administering the traditional Chinese drug monomer composition to treat *Helicobacter pylori* infection related diseases.

4. A drug for treating *Helicobacter pylori* infection related diseases, wherein an effective component is the traditional Chinese drug monomer composition according to claim 2, a mass ratio of berberine, evolitrine, and tanshinone I is 6:1:3 in the traditional Chinese drug monomer composition, and the traditional Chinese drug monomer composition has inhibitory effect on *Helicobacter pylori* and reduces drug resistance on the *Helicobacter pylori*.

* * * * *